US011118337B2

(12) United States Patent
Lloyd et al.

(10) Patent No.: US 11,118,337 B2
(45) Date of Patent: Sep. 14, 2021

(54) MOTION ACTIVATED SPRAY DISPENSER (71) Applicants: Roschell Lloyd, Iowa City, IA (US); Mohamed Karim, Iowa City, IA (US)

(72) Inventors: Roschell Lloyd, Iowa City, IA (US); Mohamed Karim, Iowa City, IA (US)

( * ) Notice: Subject to any disclaimer, the term of this patent is extended or adjusted under 35 U.S.C. 154(b) by 0 days.

(21) Appl. No.: 15/715,634

(22) Filed: Sep. 26, 2017

(65) Prior Publication Data
US 2018/0087254 A1    Mar. 29, 2018

Related U.S. Application Data (60) Provisional application No. 62/399,667, filed on Sep. 26, 2016.

(51) Int. Cl.
| E03D 9/00 | (2006.01) |
| B65D 83/26 | (2006.01) |
| B65D 83/14 | (2006.01) |
| A61L 9/14 | (2006.01) |
| B01F 13/08 | (2006.01) |
| B05B 12/02 | (2006.01) |
| B05B 15/25 | (2018.01) |

(52) U.S. Cl.
CPC .............. *E03D 9/005* (2013.01); *A61L 9/14* (2013.01); *B01F 13/0818* (2013.01); *B05B 12/02* (2013.01); *B65D 83/267* (2013.01); *B65D 83/759* (2013.01); *E03D 9/002* (2013.01); *A61L 2209/111* (2013.01); *B01F 2215/009* (2013.01); *B05B 15/25* (2018.02)

(58) Field of Classification Search
CPC . E03D 9/005; E03D 9/002; A61L 9/14; A61L 2209/111; B01F 13/0818; B01F 2215/009; B05B 12/02; B05B 15/25; B65D 83/267; B65D 83/759
USPC .................................................... 4/223
See application file for complete search history.

(56) References Cited

U.S. PATENT DOCUMENTS

| 3,617,214 | A | * | 11/1971 | Dolac | A61L 9/14 |
| | | | | | 222/180 |
| 5,168,612 | A | * | 12/1992 | Schultz | A61M 5/3278 |
| | | | | | 128/919 |
| 6,029,286 | A | * | 2/2000 | Funk | E03D 9/005 |
| | | | | | 4/223 |
| 6,321,785 | B1 | * | 11/2001 | Bergmann | E03C 1/057 |
| | | | | | 137/606 |
| 6,332,706 | B1 | * | 12/2001 | Hall | B01F 3/04794 |
| | | | | | 261/83 |
| 6,772,450 | B1 | * | 8/2004 | Saylor | E03D 9/005 |
| | | | | | 4/222 |

(Continued)

OTHER PUBLICATIONS

Reckitt Benckiser—NLB4675_SDS (Year: 2011).*

*Primary Examiner* — Benjamin R Shaw
(74) *Attorney, Agent, or Firm* — Gutwein Law; Greg N. Geiser (57) ABSTRACT

A dispensing device adapted for placement within a bathroom adjacent to a toilet to generally dispense an aerosolized fluid from within a fluid container and onto the surface of water within the toilet. The fluid is provided with a density less than water, wherein the fluid is provided to form a barrier on the surface of the water. The dispensing device including a sensor, indicator, trigger mechanism and stirring means adapted to stir the fluid within the fluid container.

14 Claims, 5 Drawing Sheets

(56) References Cited

U.S. PATENT DOCUMENTS

| | | | | |
|---|---|---|---|---|
| 8,500,044 B2* | 8/2013 | Sawalski | ............... | E03D 9/032 239/548 |
| 9,464,424 B1* | 10/2016 | Wiltshire | ............... | E03D 9/00 |
| 2006/0078461 A1* | 4/2006 | Kaplan | ............... | A61L 9/14 422/28 |
| 2007/0136937 A1* | 6/2007 | Sawalski | ............... | B65D 83/759 4/223 |
| 2007/0240252 A1* | 10/2007 | Leonard | ............... | E03D 9/032 4/223 |
| 2008/0078780 A1* | 4/2008 | Sanger | ............... | A47K 5/1217 222/1 |
| 2009/0000016 A1* | 1/2009 | Sawalski | ............... | E03D 9/032 4/223 |
| 2009/0045220 A1* | 2/2009 | Helf | ............... | B65D 83/386 222/52 |
| 2009/0249533 A1* | 10/2009 | Sawalski | ............... | E03D 9/005 4/223 |
| 2010/0038379 A1* | 2/2010 | Butler | ............... | B65D 83/267 222/52 |
| 2010/0071121 A1* | 3/2010 | Kissner | ............... | E03D 9/032 4/223 |
| 2011/0004986 A1* | 1/2011 | Vu | ............... | E03D 9/007 4/223 |
| 2011/0017769 A1* | 1/2011 | Ophardt | ............... | A47K 5/1217 222/1 |
| 2011/0088153 A1* | 4/2011 | Richard | ............... | B05B 1/20 4/223 |
| 2011/0088154 A1* | 4/2011 | Richard | ............... | E03D 9/005 4/223 |
| 2012/0131738 A1* | 5/2012 | Abbondanzio | ............... | B65D 83/388 4/223 |
| 2012/0174304 A1* | 7/2012 | Abbondanzio | ............... | E03D 9/032 4/223 |
| 2012/0211515 A1* | 8/2012 | An | ............... | A61L 9/12 222/1 |
| 2012/0211523 A1* | 8/2012 | An | ............... | A61L 9/14 222/173 |
| 2015/0210012 A1* | 7/2015 | Zenere | ............... | B29C 64/393 425/162 |
| 2015/0314032 A1* | 11/2015 | Green | ............... | B05B 11/0054 222/173 |
| 2015/0314253 A1* | 11/2015 | Cysewski | ............... | B01F 13/0818 366/273 |
| 2015/0328356 A1* | 11/2015 | Howell | ............... | B65D 83/753 222/61 |
| 2016/0211799 A1* | 7/2016 | Blick | ............... | H02S 40/38 |
| 2016/0366874 A1* | 12/2016 | Caride | ............... | A01M 1/245 |
| 2017/0259292 A1* | 9/2017 | Choi | ............... | B05B 15/70 |
| 2018/0195989 A1* | 7/2018 | Scaboo | ............... | B01F 15/00396 |
| 2019/0151811 A1* | 5/2019 | Jin | ............... | B01F 13/0827 |
| 2019/0184210 A1* | 6/2019 | Placik | ............... | A61M 16/06 |
| 2019/0307913 A1* | 10/2019 | Hsiao | ............... | A61L 9/12 |
| 2019/0360186 A1* | 11/2019 | Foss | ............... | E03D 9/005 |
| 2020/0122104 A1* | 4/2020 | Rai | ............... | B01F 15/00831 |
| 2020/0157482 A1* | 5/2020 | Levin | ............... | B01F 3/04794 |

\* cited by examiner

MOTION ACTIVATED SPRAY DISPENSER

CROSS REFERENCE TO RELATED APPLICATIONS

This application claims priority to U.S. Provisional Patent Application No. 62/399,667 filed 26 Sep. 2016 to the above named inventors, and is herein incorporated by reference in its entirety.

FEDERALLY SPONSORED RESEARCH OR DEVELOPMENT

Not Applicable

SEQUENCE LISTING, A TABLE, OR A COMPUTER PROGRAM

Not Applicable

FIELD OF THE INVENTION

The invention relates generally to a motion activated spray dispenser adapted to spray the interior of a toilet bowl prior to use.

BACKGROUND OF THE INVENTION

Within the bathroom environment it is often desired to provide users with a clean and fresh smelling space. This task is often difficult and particularly more difficult in a commercial environment with many users of the bathroom space. Traditionally, in an attempt to keep this bathroom smelling fresh, any number of chemical air freshening and fragrance devices are utilized. These air freshening and fragrance devices are generally utilized to disperse an aerosolized scent into the air of the bathroom in an attempt to mask or hide unpleasant odors. Typically, these fragrances are dispersed at a given time interval or dispersed when needed by a user after use of the bathroom facility.

More recently, a surface treatment applied to an interior surface of a toilet bowl, and more particularly to the standing water within the bowl, is used to generally form a barrier on top of the water surface to trap odor within the toilet to maintain a fresh smelling bathroom space. Traditionally, this surface treatment is applied to the water through a standard pump spray bottle utilized by a user prior to using the toilet. This method of application can generally be characterized as messy, unhygienic, and not applicable in larger volume commercial rest room facilities.

Accordingly, it would be advantageous to have a device specifically adapted to disperse a treatment within a toilet bowl on the surface of the water. Preferably, this device was automated and adapted for hands free use.

SUMMARY OF THE INVENTION

The present disclosure generally provides a device adapted to disperse an essential-oil or oil-like substance into a toilet bowl and onto the water surface within the toilet bowl to form a film-like barrier to prevent the escape of odors. The device is adapted for placement within a bathroom generally adjacent to a toilet, on a toilet, or integrated within a toilet and easily accessible to a user of the toilet. The device is provided in a mounting assembly and includes both mechanical and electrical components to ensure efficient and consistent operation. Accordingly, the device utilizes a removable container housing a barrier fluid. The barrier fluid adapted for dispensing by the device for distribution onto the surface of the water within a toilet bowl. Preferably, this barrier fluid is comprised of essential oils and formulated specifically to trap odors within the toilet.

The removable container is generally aerosolized and seated within the mounting assembly for dispersal. The mounting assembly generally includes a power source, controller, sensor, stirring means, and trigger mechanism. These components are generally coupled together in communication with the controller, wherein the controller directs the operation of the device.

The sensor is generally adapted to sense a hand swipe by a user and wherein the device is activated. Accordingly, a hand swipe will activate the trigger mechanism releasing the barrier fluid into the toilet and upon the surface water in the form of a spray. The controller is generally configured to allow a user to select a predetermined time length of spray, wherein this time is utilized to determine the amount of fluid remaining within the container of barrier fluid.

The trigger mechanism is comprised of a servo motor and lever arm in communication with a spray nozzle of the removable container and wherein the controller determines a length of time of servo engagement to control the length of spray.

The stirring means is generally utilized to stir the contents of the fluid within the removable container and generally adapted to ensure uniformity of the formulation of the barrier fluid within the removable container prior to dispensing. The stirring means utilizes a ferromagnetic pill received within the removable container and a magnetic wheel positioned with the mounting assembly adjacent to the removable container such that the magnetic wheel is in magnetic coupling with the ferromagnetic pill. Accordingly rotation of the magnetic wheel will result in rotation of the ferromagnetic pill generally agitating and stirring the fluid within the removable container. Preferably, the magnetic wheel utilizes neodymium rare earth type magnets.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

As used herein, the term "coupled" means the joining of two members directly or indirectly to one another. Such joining may be stationary in nature or movable in nature and/or such joining may allow for the flow of fluids, electricity, electrical signals, or other types of signals or communication between two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

The device of the present disclosure is generally adapted to spray a fluid from a dispenser within the interior of a toilet bowl and upon the surface of the water within the bowl to generally coat the surface of the water with a barrier layer impermeable to odors to encapsulate odor within the water. Accordingly, the device of the present disclosure can be positioned adjacent to, on, and integrated with a toilet and adapted for installation in both residential and commercial bathroom environments.

Figure 1:
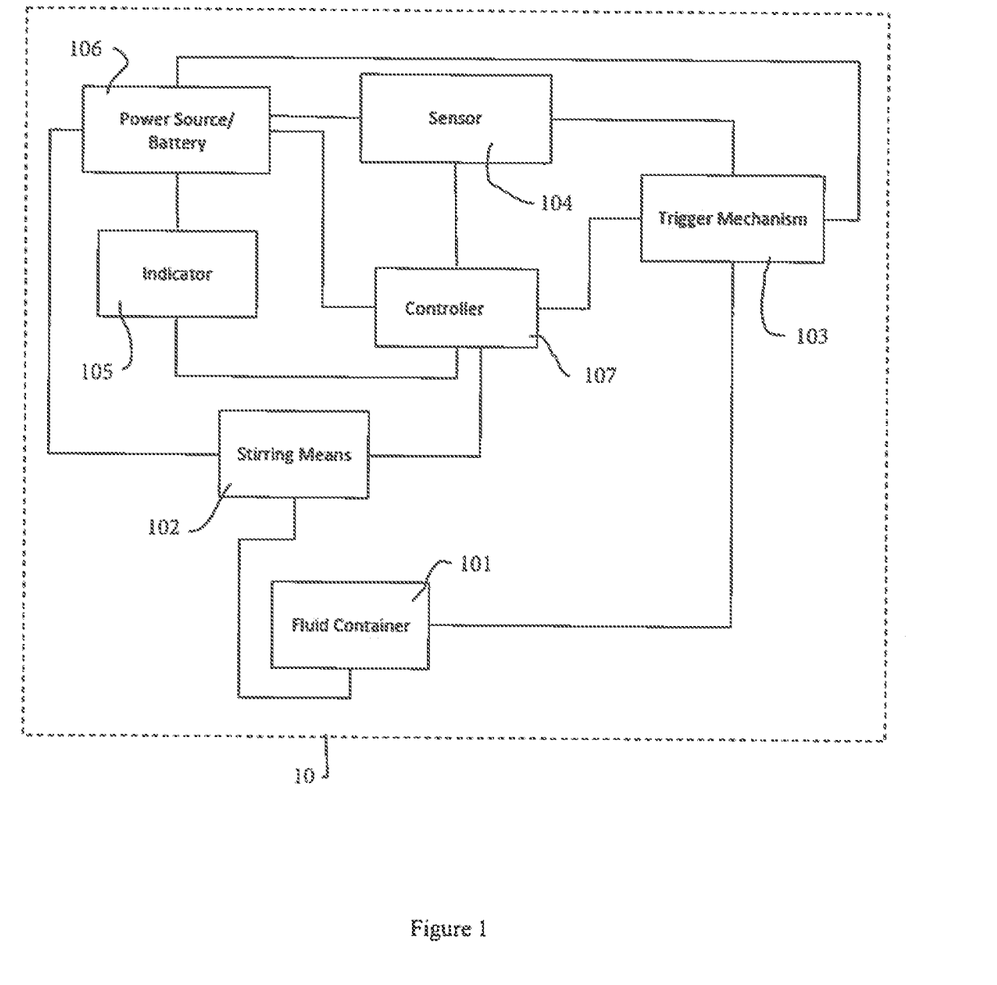
FIG. 1 shows the wire frame diagram of the control components of the device, according to the present invention.
Figure 2:
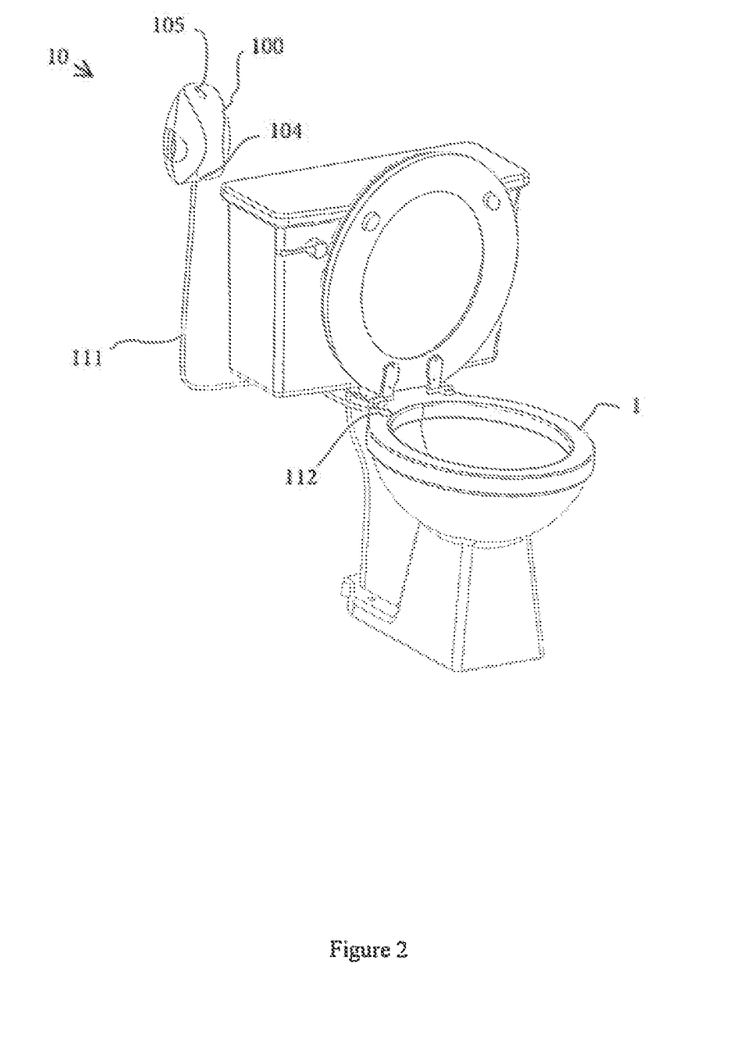
FIG. 2 is an isometric view of the device in communication with a toilet, according to the present invention.
Figure 3:
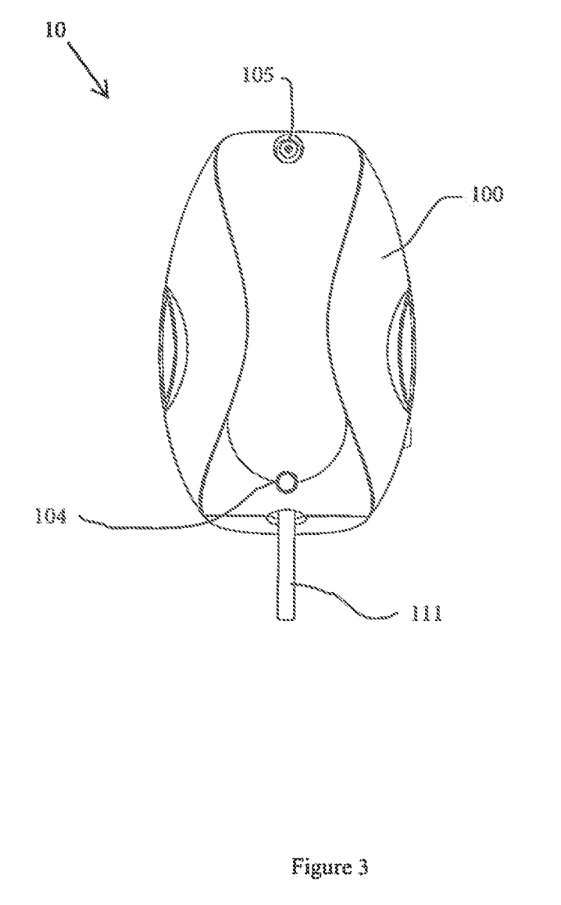
FIG. 3 is a front side external view of an embodiment of the device, according to the present invention.
Figure 4:
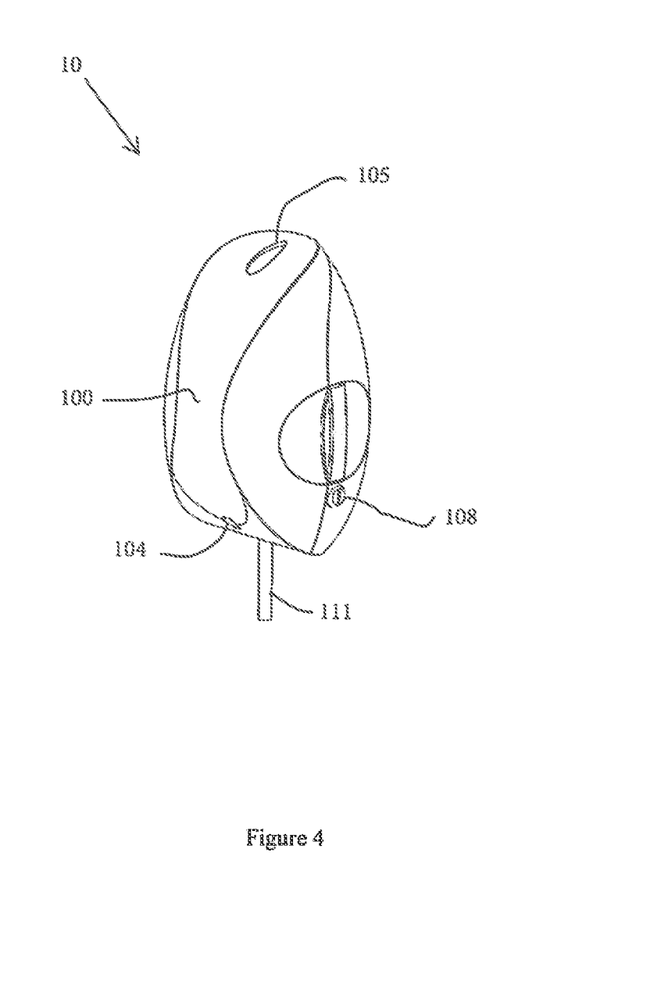
FIG. 4 is an isometric view of the embodiment of FIG. 3 of the device, according to the present invention.
Figure 5:
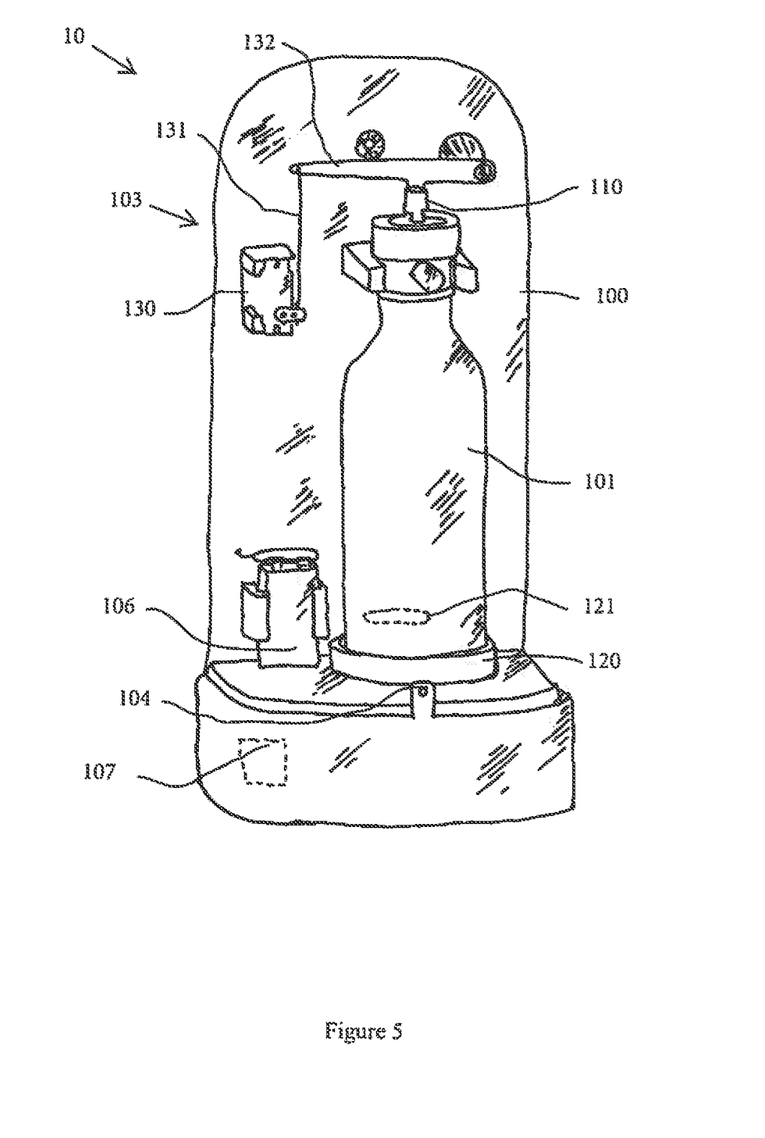
FIG. 5 is an isometric front side view of the internal components of the device, according to the present invention.

Referring to the figures, FIG. 1-FIG. 5 show a dispensing device and control mechanism for the device according to the present disclosure and generally referred to as device 10. The device 10 is comprised of a housing 100, the housing 100 enclosing the mechanical and electronic features of the device 10. These features designed to deliver a stored fluid within a removable/replaceable fluid container 101 to the surface of the water within a toilet bowl 1.

The fluid within the fluid container 101 is formulated to have a density less than water (approximately 1 $g/cm^{3)}$, wherein the fluid is adapted to float upon the surface water and specifically the standing water within a toilet bowl 1 to form a film-like barrier adapted to trap odors within the toilet bowl 1. Preferably, this formulation of fluid within the fluid container 101 is comprised of essential oil components to provide a more natural fluid.

The fluid container 101 is removed from and installed into an interior of the housing and includes a nozzle 110. The nozzle 110 is coupled to a delivery tube 111 extending opposite the housing 100 and having a spray end 112 affixed to a rim of the toilet bowl 1 adapted to disperse the fluid from the fluid container 101. The fluid container 101 is preferably a canister containing an aerosol for dispersal. Accordingly, the fluid of the disclosure is generally aerosolized for a more efficient means of propelling and dispersing the fluid into the toilet bowl 1.

The fluid within the fluid container 101 may be comprised of a formulation prone to separation and require mixing to ensure an even distribution of formulation components for maintaining the proper density. Accordingly, the housing 100 of the device 10 includes a stirring means 102. The stirring means 102 adapted to generally agitate the fluid within the fluid container 101. This agitation means may be a mechanism to generally shake the fluid container 101 prior to dispensing or preferably be a magnetic wheel 120 in magnetic coupling with a ferromagnetic pill 121 received within the fluid container 101. Accordingly, the magnetic wheel 120 is positioned adjacent the fluid container 101 and manipulated by a DC motor to rotate the magnetic wheel 120 including at least a pair of neodymium magnets aligned in polarity to generally rotate the ferromagnetic pill 121 within the container 101. Preferably, this stirring means 102 is positioned in alignment with an underside of the fluid container 101, wherein the pill 122 is generally capable of settling to a bottom of the fluid container 101 by gravity.

The dispensing of the fluid from the fluid container 101 is generally controlled by a mechanical trigger mechanism 103 coupled to the nozzle 110. The mechanical trigger mechanism 103 is comprised of a servo motor 130, linkage 131, and lever arm 132. The mechanism 103 is most generically adapted to covert a rotational force of the servo motor 130 to a linear force of the lever arm 132. The lever arm 132 is positioned adjacent to the nozzle 110 and configured to apply a downward force to a top of the nozzle 110 to release the stored fluid.

In the preferred assembly of the trigger mechanism 103 of the present disclosure, the servo motor 130 generates 25 in-oz. of rotational torque that is translated to the lever arm 132 through the linkage 131. The lever arm is approximately ½ inch in length and generally applies a linear force in a range of three (3) pounds to nine (9) pounds with the preferred torque applied to the nozzle in the range of five (5) pounds to six (6) pounds to generally activate the nozzle 110 of the fluid container 101.

The housing 100 further includes a sensor 104 adapted to sense a hand swipe by a user and generate a signal to responsively activate the trigger mechanism 103 and generally control the release of the fluid from the nozzle 110 of the fluid container 101. The sensor 104 is preferably a pyroelectric infrared (PIR) motion sensor capable of sensing a hand swipe by a user.

An indicator 105 is disposed within the housing 100 and visible from an exterior of the housing 100 to provide a status of various states of the device 10 to the user. The indicator 105 is adapted to alert a user when the device 10 is functioning properly, when a power source 106 in the form of a battery of the device 10 is low and needs to be changed, and when the fluid container 101 needs to be changed. Preferably the indicator 105 is a bi-color LED emitting light colors of green, red, and yellow to indicate these device 10 states. Preferably, the indicator 105 is programmed to display a red color when the battery is low, a green color when the device is operating according to normal, and yellow when the fluid container 101 needs to be replaced. Accordingly, the indicator 105 may flash both red and yellow when the battery is low and the fluid container 101 needs to be replaced.

The power source 106 of the device 10 is replaceable and preferably in the form of a 9V battery. Although a 9V battery is preferred for the power source 106, other power sources in the form of both different battery sizes and types and a direct connection to a power source, such as an alternating current wall receptacle, may be utilized.

The device 10 utilizes a controller 107 to generally control the various mechanical and electrical systems of the device 10. The controller 107 is coupled to the trigger mechanism 103, the sensor 104, the power source 106, the indicator 105, and the stirring means 102. The controller 107 is preferably programmed with Arduino software and capable of serial communication to the various drivers and systems of the device. The logic of the controller 107 is generally provided to check the battery 106 level of the device 10, count the length of time of a given spray from the fluid container 101 operated by the trigger mechanism 103, and indicate the status of the device 10 with the indicator 105. The controller 107 will use the counter to determine when a fluid container 101 needs to be changed by tracking the total amount of dispensing time against a predetermined amount of time related to the amount of fluid provided within the fluid container 101.

The device 10 may be provided with a button to allow for a purge and priming of the tube 111 spray end 112 to ensure adequate spray. Further, the device 10 may include a potentiometer to adjust the amount of time for the dispensing of the fluid from the fluid container 101. Preferably, this potentiometer allows for adjust within the range of one (1) second to six (6) seconds.

The housing 100 may be secured through a lock mechanism 108. The lock mechanism 108 securing the housing 100 and the internal components of the device 10 and restricting access to these components. The lock mechanism 108 is preferably opened with a key and utilized in a commercial environment.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

The invention claimed is:

1. A dispensing device adapted for placement adjacent to a toilet, the dispensing device comprising:
   a fluid container, the fluid container containing a fluid having a density less than the density of water, the fluid container having a nozzle, the nozzle in communication with an interior of the toilet;
   a stirring means, the stirring means adapted to agitate the fluid within the fluid container;
   a sensor, the sensor configured to generate a signal upon a hand swipe of a user; and
   a trigger mechanism, the trigger mechanism coupled to the sensor and the nozzle of the fluid container, wherein the trigger mechanism opens the nozzle for the release of fluid from the fluid container into the toilet upon receipt of the signal.

2. A dispensing device in communication with a toilet, the dispensing device comprising:
   a fluid container, the fluid container containing an aerosolized fluid having a density less than the density of water, the fluid container having a nozzle, the nozzle in communication with an interior of the toilet;
   a ferromagnetic pill, the ferromagnetic pill received within an interior of the fluid container and within the aerosolized fluid;
   a sensor, the sensor configured to generate a signal upon a hand swipe of a user;
   a trigger mechanism, the trigger mechanism coupled to the sensor and the nozzle of the fluid container, wherein the trigger mechanism opens the nozzle for the release of fluid from the fluid container into the toilet upon receipt of the signal;
   a stirring means, the stirring means including a magnetic wheel positioned adjacent to the fluid container and adapted for rotation, the magnetic wheel in magnetic coupling with the ferromagnetic pill, wherein rotation of the magnetic wheel correspondingly rotates the ferromagnetic pill;

a power source, the power source providing power to the dispensing device;

an indicator, the indicator configured to display a status of the device related to the power source and an amount of fluid within the fluid container;

a controller, the controller coupled to the sensor, the trigger mechanism, the power source, the indicator, and the stirring means, wherein the controller directs the release of the aerosolized fluid from the fluid container upon the signal; and a housing, the housing enclosing the device.

3. The dispensing device of claim 2, wherein the sensor is an infrared sensor.

4. The dispensing device of claim 2, wherein the indicator is a light emitting diode.

5. The dispensing device of claim 2, wherein the fluid within the fluid container comprises at least one essential oil.

6. The dispensing device of claim 2, wherein the power source is a removable battery.

7. The dispensing device of claim 6, wherein the power source is a nine volt battery.

8. The dispensing device of claim 2, wherein the nozzle is coupled to a tube extending from the nozzle a length and culminating in a spray end, the spray end received on a rim of the toilet and adapted to direct the fluid from the fluid container onto a surface of the water within the toilet bowl.

9. The dispensing device of claim 2, wherein the trigger mechanism includes a servo motor, a lever arm coupled to the nozzle, and a linkage connecting the servo motor and the lever arm.

10. The dispensing device of claim 2, wherein the stirring means includes a direct current motor, the direct current motor rotating the magnetic wheel.

11. The dispensing device of claim 10, wherein the magnetic wheel includes at least a pair of neodymium magnets.

12. A dispensing device in communication with a toilet, the toilet having a bowl and rim portion containing standing water, the dispensing device comprising:

a fluid container, the fluid container containing an aerosolized fluid having a density less than the density of water, the fluid container having a nozzle, the nozzle in communication with an interior of the toilet;

a ferromagnetic pill, the ferromagnetic pill received within an interior of the fluid container and within the aerosolized fluid;

a sensor, the sensor being infrared and configured to generate a signal upon a hand swipe of a user;

a trigger mechanism, the trigger mechanism coupled to the sensor and the nozzle of the fluid container, wherein the trigger mechanism opens the nozzle for the release of fluid from the fluid container into the toilet upon receipt of the signal;

a stirring means, the stirring means including a magnetic wheel positioned adjacent to the fluid container and adapted for rotation, the magnetic wheel having at least a pair of neodymium magnets in magnetic coupling with the ferromagnetic pill, wherein rotation of the magnetic wheel correspondingly rotates the ferromagnetic pill;

a power source, the power source removable and providing power to the dispensing device;

an indicator, the indicator of the light emitting diode type and configured to display a status of the device related to the power source and an amount of fluid within the fluid container;

a controller, the controller coupled to the sensor, the trigger mechanism, the power source, the indicator, and the stirring means, wherein the controller directs the release of the aerosolized fluid from the fluid container upon the signal; and a housing, the housing enclosing the device.

13. The dispensing device of claim 12, wherein the fluid within the fluid container comprises at least one essential oil.

14. The dispensing device of claim 13, wherein the nozzle is coupled to a tube extending from the nozzle a length and culminating in a spray end, the spray end received on the rim of the toilet and adapted to direct the fluid from the fluid container onto the surface of the water within the toilet bowl.

* * * * *